United States Patent
Pona

(10) Patent No.: US 8,162,661 B2
(45) Date of Patent: Apr. 24, 2012

(54) ULTRASONIC CROWN AND BRIDGE REMOVER

(76) Inventor: Zbigniew Pona, Windsor (CA)

( * ) Notice: Subject to any disclaimer, the term of this patent is extended or adjusted under 35 U.S.C. 154(b) by 251 days.

(21) Appl. No.: 11/783,329

(22) Filed: Apr. 9, 2007

(65) Prior Publication Data

US 2008/0248446 A1 Oct. 9, 2008

(51) Int. Cl.
*A61C 3/00* (2006.01)
*A61C 1/07* (2006.01)
*A61C 3/03* (2006.01)
*A61C 3/08* (2006.01)
*B25B 1/00* (2006.01)
*B25B 1/06* (2006.01)

(52) U.S. Cl. .......... 433/119; 433/4; 269/6; 269/254 CS

(58) Field of Classification Search .......... 433/118–119, 433/102, 224, 165, 141, 166, 152–160, 86, 433/218–223, 4; 606/205–208; 269/86, 269/87, 89, 90, 91, 92, 96, 98, 104, 107, 269/126, 128, 129, 3, 6, 149, 249, 254 CS; 81/300–312, 342, 94, 97, 99, 117

See application file for complete search history.

(56) References Cited

U.S. PATENT DOCUMENTS

| | | | | |
|---|---|---|---|---|
| 560,419 A | * | 5/1896 | Markowsky | 433/146 |
| 1,380,726 A | * | 6/1921 | Lurie | 433/157 |
| 1,498,285 A | * | 6/1924 | Lorenz | 433/154 |
| 1,634,058 A | * | 6/1927 | Teragawa | 433/151 |
| 1,858,080 A | * | 5/1932 | Flagstad et al. | 433/154 |
| 2,627,113 A | * | 2/1953 | Moray | 433/154 |
| 3,754,331 A | * | 8/1973 | Agnone | 433/160 |
| 3,827,148 A | * | 8/1974 | Diliberto | 433/122 |
| 5,257,558 A | * | 11/1993 | Farzin-Nia et al. | 81/418 |
| 5,320,532 A | | 6/1994 | Farzin-Nia et al. | |
| 5,451,161 A | * | 9/1995 | Sharp | 433/119 |
| 5,547,380 A | * | 8/1996 | Goodman | 433/215 |
| 5,733,119 A | | 3/1998 | Carr | |
| 6,190,167 B1 | * | 2/2001 | Sharp | 433/119 |
| 6,282,995 B1 | * | 9/2001 | Lin | 81/423 |
| 6,413,088 B1 | * | 7/2002 | Kawaguchi | 433/159 |
| 7,165,970 B2 | * | 1/2007 | Anderson | 433/159 |
| 2003/0003418 A1 | * | 1/2003 | Kumabe | 433/119 |
| 2005/0272006 A1 | * | 12/2005 | Rosenberg | 433/159 |

FOREIGN PATENT DOCUMENTS

| | | | |
|---|---|---|---|
| DE | 4109988 | * | 3/1991 |
| DE | 4109988 | * | 10/1992 |
| WO | WO2008003144 | * | 1/2008 |

\* cited by examiner

*Primary Examiner* — Todd Manahan
*Assistant Examiner* — Yogesh Patel
(74) *Attorney, Agent, or Firm* — Warn Partners, P.C.

(57) ABSTRACT

A dental tool having a pair of releasably and pivotably connected opposing jaw members. A biasing mechanism connected to at least one of the jaw members biases the jaw members toward a proximate rest position. A separating mechanism is connected to at least one jaw member for separating the jaw members. An ultrasonic vibrator is connected to the jaw members for vibrating them. A fastening device may be used to connect the pair of opposing jaw members.

12 Claims, 4 Drawing Sheets

ULTRASONIC CROWN AND BRIDGE REMOVER

FIELD OF THE INVENTION

In one of its aspects, the present invention relates to a vibrating dental tool for the removal of crowns and bridges.

BACKGROUND OF THE INVENTION

Vibrating dental tools and, in particular, ultrasonic dental tools are known.

U.S. Pat. No. 5,320,532 (Farzin-Nia et al.) teaches an ultrasonic tool for fracturing the interface between dental structures and, specifically, for the removal of orthodontic bands or brackets from teeth after the completion of treatment. The working tip of the tool may be wedge-shaped, flat or needle shaped. In one embodiment, a pair of spaced projections are disposed on either side of an engaging surface to provided a receiving area for the bracket to minimize slipping off. In use, the tip of the tool is placed against a bracket and ultrasonic energy is transferred through the bracket to the adhesive layer.

U.S. Pat. No. 5,733,119 (Carr) teaches a microsurgical drill bit, which can be connected to an ultrasonic transducer. The drilling tips are angled and may have bent end portions to permit the tool to be held at a comfortable angle.

While drilling devices and simple devices for the removal of adhesively connected dental structures are known, there is a need for a dental tool adapted for the removal of crowns and bridges.

The crowning and bridging of teeth is a common practice in dentistry. There are a number of indications for crowns and bridges. Some of the more common indications are: heavily restored teeth with little of the original teeth left; following root canal treatments; and bridges for the replacement of missing teeth. Crowns and bridges may also be used for aesthetic reasons.

When a tooth is prepared for a crown, the practitioner removes or shaves off the surface of the tooth to a depth of approximately 1.5 millimeter (mm). The practitioner generally then cements a temporary crown to the tooth. The practitioner then generally awaits lab work on the tooth, before cementing in a permanent crown.

There are many instances where a practitioner must remove a crown or bridge. One common instance is the removal of a temporary crown. This may prove particularly challenging where the temporary crown fits tightly over the original tooth. Another common instance is the removal of a permanent crown that has been temporarily cemented. This might occur, for example, where the practitioner wishes to obtain approval of the crown from the patient before permanently securing it. This might also occur where the practitioner wishes to ensure that tooth sensitivity will subside before permanently securing a crown.

Other common instances may arise after a crown has been permanently secured. For example, removal of a crown is required where there is caries underneath it and the practitioner does not wish to cut the crown to provide treatment. Similarly, a crown may need to be removed where it is necessary to perform a root canal on the underlying tooth. Yet another instance might be where one crown of a bridge becomes loose and the practitioner must remove the other crowns of the bridge in order to re-cement the bridge.

Existing crown removal tools generally involve the application of a blunt force to the crown, which often results in broken or fractured crowns or teeth. This can add complexity and expense to a dental procedure and, in addition, may cause additional discomfort to a patient. The inventor is aware of an ultrasonic crown removal tool, the ATD Automatic Crown & Bridge Remover by J. Morita, USA, Inc. This tool consists of ultrasonic steel string arranged as a loop and a pneumatic hook that attaches to a hand piece that causes slow movement of the hook. The steel string, while designed to assist with separating the crown from the root, suffers from a number of drawbacks. The steel string is difficult to position if the teeth are close together. Further, if the crown-tooth interface is smooth, the string will not catch at this position. The string also has trouble penetrating the crown-tooth junction. Finally, due to the application of pressure on one side of the crown or tooth-crown junction, the crown almost invariably breaks during the removal procedure, which adds to the complexity and expense of the procedure.

SUMMARY OF THE INVENTION

It is an object of the present invention to obviate or mitigate at least one of the above-mentioned disadvantages of the prior art.

Accordingly, in one of its aspects, the present invention provides a dental tool, comprising: a pair of opposing jaw members; a biasing mechanism connected to a jaw member for biasing the jaw members toward a proximate rest position; a separating means connected to a jaw member for separating the jaw members; a vibrator connected to the jaw members for vibrating them; and securing means connecting the pair of opposing jaw members.

BRIEF DESCRIPTION OF THE DRAWINGS

Embodiments of the present invention will be described with reference to the accompanying drawings, wherein like reference numerals denote like parts, and in which.

DETAILED DESCRIPTION OF THE PREFERRED EMBODIMENTS

Figure 1:
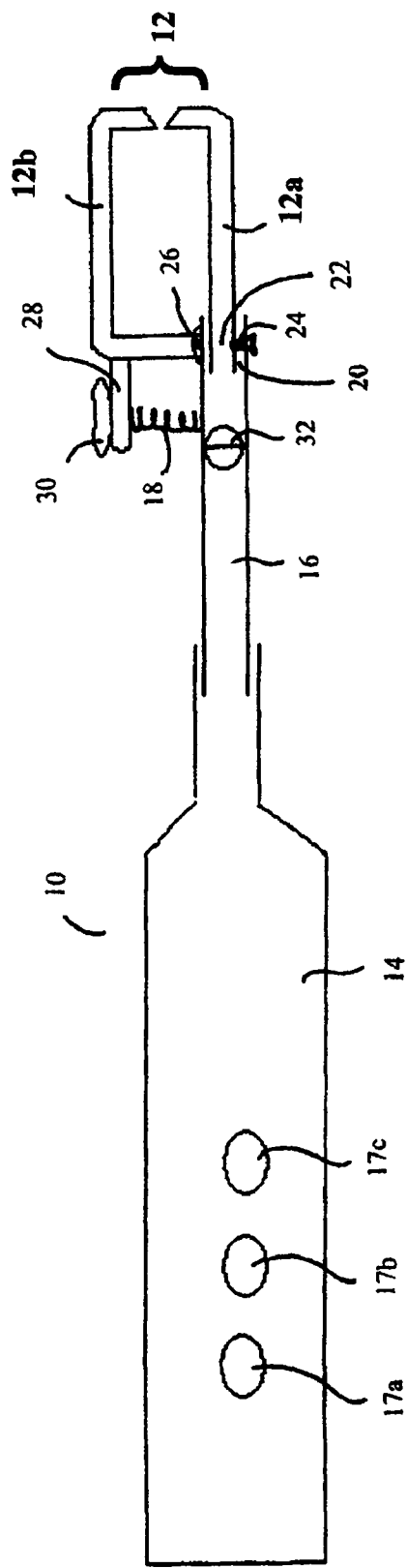
FIG. 1 illustrates a front view of an embodiment of the present dental tool in the rest position.

With reference to FIG. 1, dental tool 10 has a pair of opposed jaw members 12. Jaw members 12a and 12b are connected to a handle 14 through a neck 16.

Preferably, handle 14 contains a vibrator, preferably in the form of an ultrasonic transducer for vibrating jaw members 12a and 12b. In an alternate embodiment, handle 14 may be connected to an ultrasonic transducer and handle 14 may contain means for transferring movement or vibrations to jaw members 12a and 12b. A power source for the ultrasonic transducer may be housed in handle 14, preferably in the form of batteries. In an alternate embodiment, handle 14 may have means for connecting to an external power source. Ultrasonic dental handles or transducer heads are commonly used in the art in conjunction with cleaning tips. The particular configuration of the handle is not restricted and is within the purview of a person skilled in the art. Generally speaking handle 14 must have a motor (not shown) connected to the power sources (e.g. batteries), to the jaw members 12 for driving them, and to switching means for controlling the operation of the motor.

Preferably, manually operable control buttons 17a, 17b, and 17c are provided on handle 14 for powering dental tool 10 on and off and for varying the power supplied to jaw members 12a and 12b, thereby varying their amplitude of vibration. Preferably, one control button provides a high power setting, while a second control button provides a low power setting. The number of power settings is not particularly restricted and is within the purview of a person skilled in the art. Rather than discrete power settings, the power may be adjustable along a spectrum.

Suitable vibrational frequencies are within the purview of a person skilled in the art. The vibrator may suitably vibrate at between about 15,000 and about 40,000 Hertz. More preferably, the vibrator vibrates between about 20,000 and about 30,000 Hertz. Most preferably, the vibrator vibrates between about 25,000 and 28,000 Hertz.

Jaw members 12a and 12b are biased toward each other by biasing means, preferably in the form of a spring 18. As will be apparent to a person skilled in the art, the position and number of biasing means is not particularly restricted, there may, for example, be a pair of biasing means, one operating on each of jaw members 12a and 12b. Generally, in the proximate rest position there will be a small space between jaw members 12a and 12b, typically of about 1 mm (although the space may be larger or jaw members 12a and 12b may be touching).

Neck 16 preferably has a hollow tubular portion 20 for slidably receiving a rear leg portion 22 of a first jaw member 12a having a substantially L-shape. The rear leg portion 22 extends longitudinally from the neck 16 having the same longitudinal axis. Preferably, adjustment and securing means are provided for adjusting the position of rear leg portion 22 within tubular portion 20 and for securing it in position, once the desired position is obtained. Suitable adjustment and securing means include a screw 24 that can be tightened to frictionally engage rear leg portion 22. Tubular portion 20 may have one or more apertures or a continuous slot for receiving screw 24. Similarly, rear leg portion 22 could have apertures therein for receiving securing means. In an alternate embodiment, screw 24 may be replaced by a biased pin (now shown) receivable in one of a series of apertures for securing leg portion 22 is a desired position.

Various adjustment and securing means will be apparent to a person skilled in the art. It will be apparent that the securing mechanisms must be fairly strong and reliable to maintain the position of jaw member 12a during operation.

A second jaw member 12b having a substantially C-shape is pivotally attached to an exterior of neck 16 at pivot point 26 substantially perpendicular to the longitudinal axis of the neck 16 and rear leg portion 22. In the embodiment shown, second jaw member 12 b has an extended rear leg portion 28 extending rearward substantially parallel to the longitudinal axis of the neck 16 when the first and second jaw members 12a, 12b are in a substantially closed position. Spring 18 is secured between extended rear leg portion 28 and neck 16 and has a longitudinal axis substantially perpendicular to the longitudinal axis of the neck 16. Spring 18 may be secured to one or both of neck 16 and extended rear leg portion 28. Various mechanisms for securing spring 18 will be apparent to persons skilled in the art and include for example hooking the ends to small apertures in the respective parts. In a preferred embodiment, neck 16 may have protruding walls 29 connected by a freely rotating pin 31 which in turn passes through a portion of extended rear leg portion 28, permitting rear leg portion 28 to freely rotate about the pin.

Figure 2:
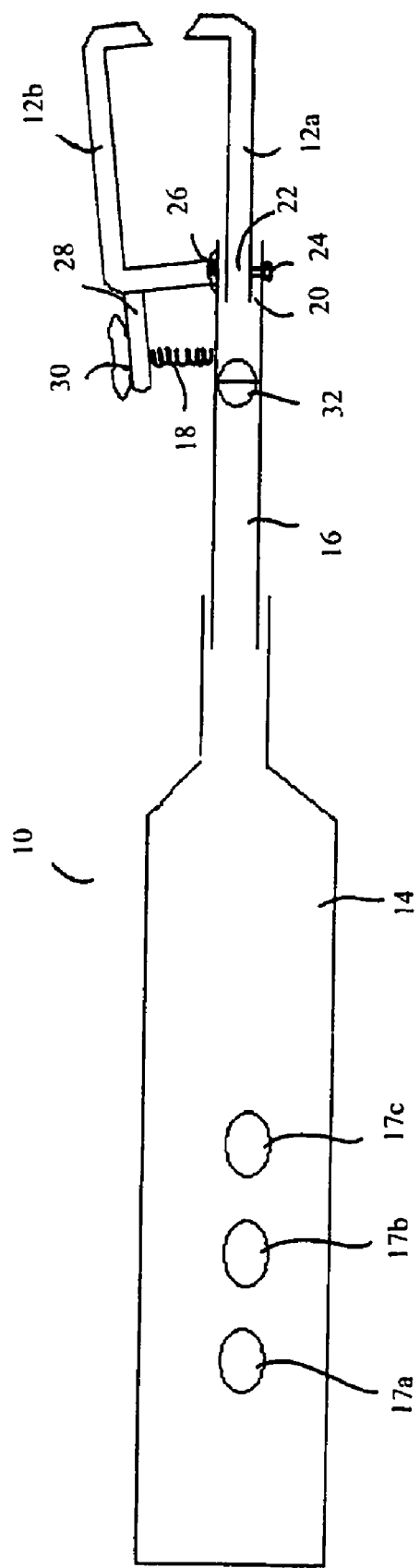
FIG. 2 illustrates a front view of an embodiment of the present dental tool in an open position.

With reference to FIG. 2, extended rear leg portion 28 preferably has a manually depressible actuator 30. Depression of actuator 30 downward in the direction toward the neck 16 overcomes spring 18, permitting jaw members 12a and 12b to open. Upon release of actuator 30, spring 18 forces jaw members 12a and 12b toward a proximate rest position. In practice, generally a practitioner will depress actuator 30 using his or her thumb.

Neck 16 is preferably detachably secured to handle 14. Neck 16 may be secured to handle 14 by any suitable means. The securing means is preferably in the form of a threaded socket in handle 14 (not shown) with corresponding threads on neck 16. Other suitable securing means include, for example, a bayonet lock or a tool chuck. Jaw members 12a and 12b may also be detachably secured to neck 16. This arrangement facilitates cleaning of dental tool 10. In particular, neck 16, rear leg portions 22 and 28 and jaw members 12a and 12b can advantageously be sterilized as a single unit.

Preferably, neck 16 has an internal pivot point 32 to selectively secure the first and second jaw members 12a and 12b at a predetermined angled position. Neck 16 may have a plurality of pivot points. The number and position of internal pivot points in neck 16 is not particularly restricted and is within the purview of a person skilled in the art. Internal pivot point 32 facilitates placement of jaw members 12a and 12b, within the mouth of a patient. In particular, this facilitates use of tool 10 on posterior upper molars and posterior lower molars. Neck 16 may further include releasable locking means for locking the position of internal pivot point 32 so as to impart a specific angle to neck 16 for use. The amount of force required to pivot about internal pivot point 32 may be selected so that pivoting can be performed manually or with the assistance of a tool. A locking mechanism (not shown) can be provided to prevent pivoting of neck 16 during use of dental tool 10 is unlikely. Various suitable locking mechanisms will be apparent to a person skilled in the art. Suitable mechanisms include a pin and sprocket mechanism (not shown) whereby an actuator is provided for disengaging the pin from the sprocket and permitting free pivoting and where upon release of the actuator, the pin engages the sprocket, thereby securing neck 16 at a desired internal angle. Another suitable locking mechanism would be interlocking members (not shown) that may be secured in a number of angled positions and that can be locked in a desired position using an actuable mechanism.

Figure 3:
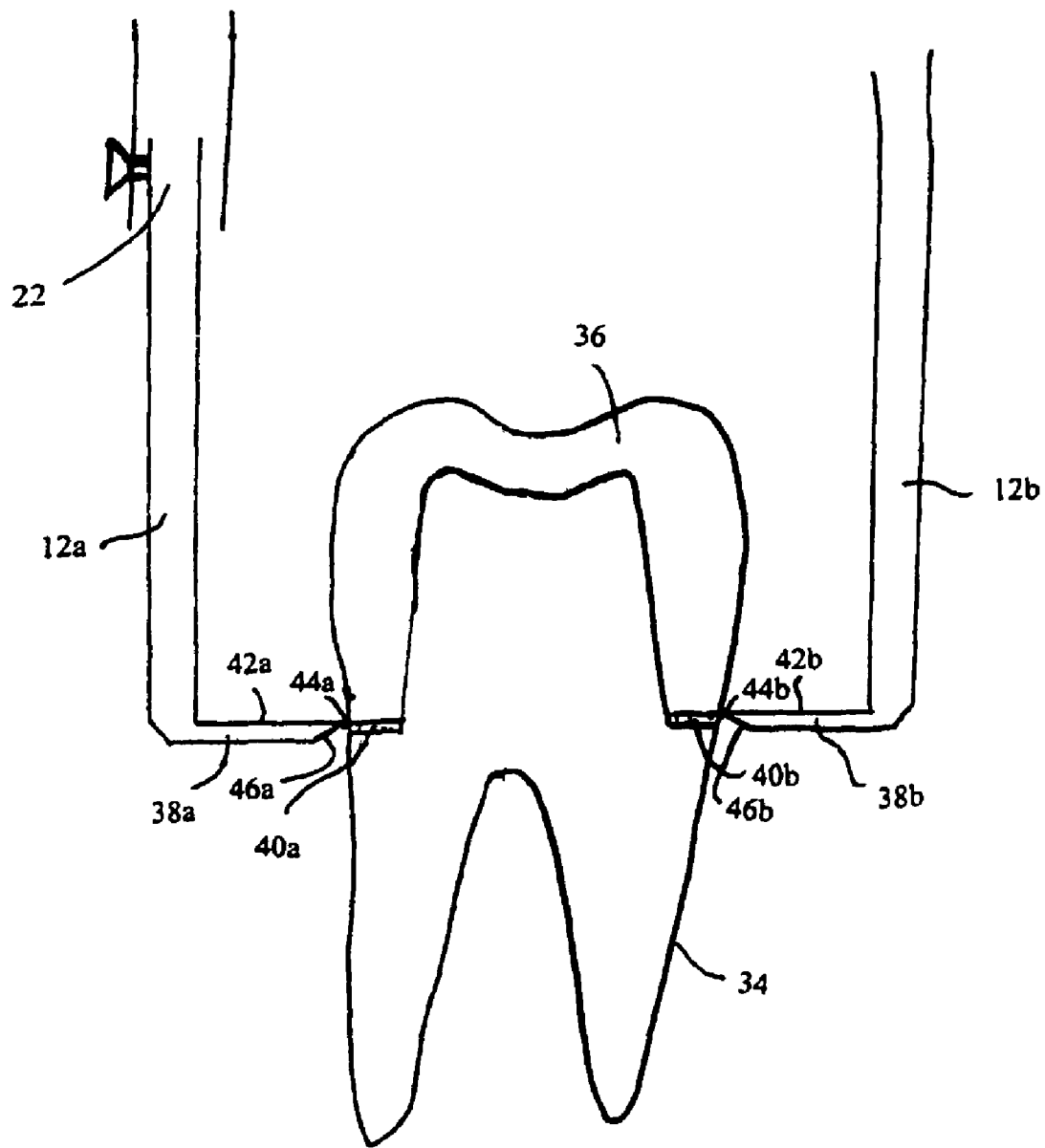
FIG. 3 illustrates an enlarged partial front view of an embodiment of the present dental tool being positioned on a tooth.

With reference to FIGS. 2 and 3, there is shown a tooth 34, having a crown 36 thereon. Dental tool 10 is positioned so as to effect removal of a crown 36. In practice, the practitioner depresses actuator 30 so as to open jaw members 12a and 12b. The position of rear leg portion 22 of first jaw member 12a may be adjusted to accommodate a crown 36 that is longer on one side than the other, as shown in FIG. 3. The practitioner places open jaw members 12a and 12b about tooth 34 so that front wedge portions 38a and 38b are positioned at tooth-crown interface 40a and 40b. Each front wedge portion 38a and 38b preferably has a substantially flat inner surface 42a and 42b for engaging the underside of crown 36 at tooth-crown interface 40a and 40b. Once tool 10 is positioned, the practitioner turns on the ultrasonic vibrations using the appropriate control button(s) 17a, 17b and/or 17c.

Preferably, tips 44a and 44b of wedge portions 38a and 38b are sharp edges. Alternately, tips 44a and 44b may taper to a sharp point. Tips 44a and 44b of wedge portions 38a and 38b are shaped to facilitate wedging of wedge portions 38a and 38b between crown 36 and tooth 34. The shape of tips 44a and 44b also helps wedge portions 38a and 38b to chip into cement at tooth-crown interface 40a and 40b. Spring 18 applies pressure to tips 44a and 44b of wedge portions 38a and 38b as it forces jaw members 12a and 12b toward the proximate rest or closed position.

The outer surfaces 46a and 46b of wedge portions 38a and 38b are angled. This angled outer surfaces 46a and 46b facilitates prying into cement and the forcing of crown 36 from tooth 34.

Figure 4:
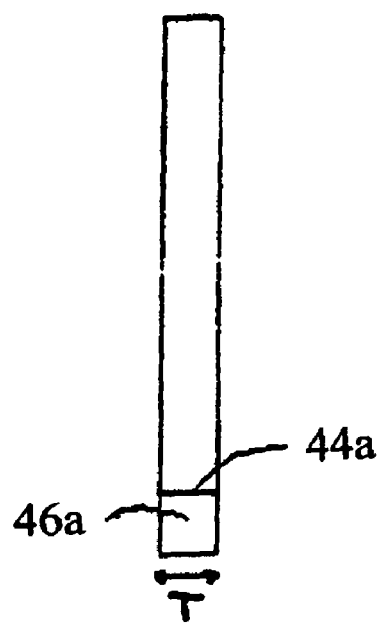
FIG. 4 illustrates a magnified side view of a wedge portion of an embodiment of the present dental tool.
Figure 5:
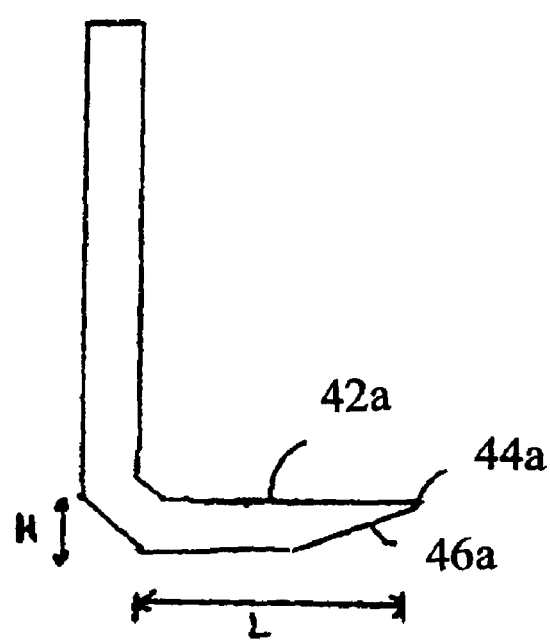
FIG. 5 illustrates a magnified front view of a wedge portion of an embodiment of the present dental tool.

Preferably, wedge portion 38 is about 0.5 to 2.5 mm thick, as shown by the letter T in FIG. 4. More preferably, wedge portion 38 is about 1 mm thick. Preferably, inner surface 42 of wedge portion 38 is between about 4 and 8 mm in length and more preferably about 6.5 mm in length, as shown by the letter L in FIG. 5; this length generally being slightly longer than the thickness of a typical crown. The height of wedge portion 38, as shown by the letter H in FIGS. 4 and 5 is preferably between about 0.5 and about 2 mm, and more preferably about 1 mm.

Preferably, in use, a low power setting would be used initially to insert wedge portions 38a and 38b between tooth 34 and crown 36 in order to provide a good grip into tooth-crown interface 40a and 40b and then a high power setting would preferably be used to remove crown 36, thereby minimizing the amount of trauma caused by the procedure.

Jaw members 12a and 12b are preferably formed of a strong, durable, substantially rigid and substantially heat-resistant medical grade material, such as stainless steel or a titanium alloy.

Preferably, the surfaces of wedge portions 38a and 38b are relatively smooth to facilitate sliding placement of wedge portion 38 into tooth-crown interface 40a and 40b. It is, however, known in the art to coat the surfaces of dental tools with a fine layer of material that imparts additional strength and/or abrasiveness. In particular, a thin layer of diamonds is preferred for this purpose. In the case of dental tool 10, such a fine diamond layer is suitably applied to tips 44a and 44b and/or outer surfaces 46a and 46b for chipping away of the cement. Such a thin layer of diamonds might also suitably be applied to flat inner surfaces 42a and 42b to facilitate engagement of inner surfaces 42a and 42b against crown 36.

While this invention has been described with reference to illustrative embodiments and examples, the description is not intended to be construed in a limiting sense. Thus various modifications of the illustrative embodiments, as well as other embodiments of the invention, will be apparent to persons skilled in the art upon reference to this description.

The invention claimed is:

1. An ultrasonic, vibrating dental tool for removing a dental crown, comprising:
a handle having a longitudinal axis and a neck portion extending longitudinally therefrom having the same longitudinal axis;
a first jaw member releasably connected to the neck portion having a substantially L-shape and having a rear leg portion extending longitudinally from the neck portion, said rear leg portion is slidably received within the neck portion for selectively positioning of the first jaw member for engaging a dental crown;
a second jaw member releasably connected to the neck portion having a substantially C-shape that is pivotably connected at a pivot point to the neck portion substantially perpendicular to the longitudinal axis of the neck portion and rear leg portion of the first jaw member, and having an extended rear leg portion extending rearward substantially parallel to the longitudinal axis of the neck portion when the jaw members are in a substantially closed position;
a biasing member connected to the neck portion and the extended rear leg portion of the second jaw member having a longitudinal axis substantially perpendicular to the longitudinal axis of the neck portion, the biasing member operable to bias the jaw members to the closed position;
a depressible actuator connected to the biasing member, operable to open the jaw members when compressed downward in the direction toward the neck portion, the actuator operable to pivot the second jaw member about the pivot point;
at least one internal pivot point in the neck portion to selectively secure the first and second jaw members at a predetermined angled position;
the first and second jaw members being substantially parallel to each other, each jaw member having a front wedge portion for engaging the dental crown, the front wedge portion being operable to engage a crown therebetween, the end of each front wedge portion having an angled outer surface to facilitate removal of the crown; and
a vibrator, located within the handle, and operable to vibrate the jaw members.

2. The dental tool defined in claim 1, wherein the actuator is a manually operated actuator, depression of which separates the jaw members.

3. The dental tool defined in claim 1, wherein the neck portion comprises a fastening device for releasably connecting the pair of jaw members to the neck portion.

4. The dental tool defined in claim 3, further comprising an adjustment mechanism for adjusting the connection of at least one jaw member to the neck portion.

5. The dental tool defined in claim 1, wherein the outer surface is abrasive.

6. The dental tool defined in claim 1, wherein the jaw members are formed of stainless steel.

7. The dental tool defined in claim 1, wherein the jaw members are formed of a titanium alloy.

8. The dental tool defined in claim 1, wherein the vibrator is an ultrasonic transducer.

9. The dental tool defined in claim 1, wherein the vibrator vibrates at between about 15,000 and 40,000 Hertz.

10. The dental tool defined in claim 1, wherein the vibrator vibrates at between about 20,000 and 30,000 Hertz.

11. The dental tool defined in claim 1, wherein the vibrator vibrates at between about 25,000 and 28,000 Hertz.

12. The dental tool defined in claim 1, further comprising a mechanism for adjusting the amplitude of vibration of the vibrator.

* * * * *